US008877974B2

(12) United States Patent
Hell et al.

(10) Patent No.: US 8,877,974 B2
(45) Date of Patent: Nov. 4, 2014

(54) PROCESS FOR THE PREPARATION OF (1R,2R)-3-(3-DIMETHYLAMINO-1-ETHYL-2-METHYLPROPY1)-PHENOL

(75) Inventors: Wolfgang Hell, Aachen (DE); Oswald Zimmer, Wuerselen (DE); Helmut Heinrich Buschmann, Sant Just Desvern (ES); Joerg Holenz, Enhoerna (SE); Stefan Gladow, Buchs (CH)

(73) Assignee: Grünenthal GmbH, Aachen (DE)

( * ) Notice: Subject to any disclaimer, the term of this patent is extended or adjusted under 35 U.S.C. 154(b) by 1375 days.

(21) Appl. No.: 12/374,874

(22) PCT Filed: Jul. 23, 2007

(86) PCT No.: PCT/EP2007/006515
§ 371 (c)(1),
(2), (4) Date: Oct. 22, 2009

(87) PCT Pub. No.: WO2008/012047
PCT Pub. Date: Jan. 31, 2008

(65) Prior Publication Data
US 2010/0099916 A1    Apr. 22, 2010

(30) Foreign Application Priority Data
Jul. 24, 2006  (EP) .................................... 06015338

(51) Int. Cl.
C07C 215/00   (2006.01)
C07B 57/00    (2006.01)
C07C 213/00   (2006.01)
C07C 213/08   (2006.01)

(52) U.S. Cl.
CPC ............... *C07B 57/00* (2013.01); *C07C 213/00* (2013.01); *C07C 213/08* (2013.01)
USPC ........................................................ 564/355

(58) Field of Classification Search
None
See application file for complete search history.

(56) References Cited

U.S. PATENT DOCUMENTS

| 4,012,456 | A | 3/1977 | Chaplits |
| 4,276,195 | A | 6/1981 | Verkade |
| 4,889,777 | A | 12/1989 | Akuto |
| 5,565,594 | A | 10/1996 | Spindler et al. |
| 5,583,241 | A | 12/1996 | Spindler |
| 5,783,715 | A | 7/1998 | Pugin |
| 5,811,582 | A | 9/1998 | Buschmann et al. |
| 6,203,939 | B1 | 3/2001 | Wilson |
| 6,248,737 | B1 | 6/2001 | Buschmann et al. |
| 6,372,387 | B1 | 4/2002 | Kawakami et al. |
| 6,890,959 | B2 | 5/2005 | Puetz et al. |
| 7,417,170 | B2 | 8/2008 | Hell et al. |
| 7,589,196 | B2 | 9/2009 | Pugin et al. |
| 2002/0010178 | A1 | 1/2002 | Buschmann et al. |
| 2002/0074972 | A1 | 6/2002 | Narang et al. |
| 2003/0092773 | A1* | 5/2003 | Evans ........................... 514/650 |
| 2004/0106046 | A1 | 6/2004 | Inda |
| 2004/0191630 | A1 | 9/2004 | Kawamura et al. |
| 2006/0167318 | A1 | 7/2006 | Jagusch et al. |
| 2006/0194988 | A1 | 8/2006 | Hell et al. |
| 2010/0009916 | A1 | 1/2010 | Bokvist et al. |

FOREIGN PATENT DOCUMENTS

| CA | 2170100 A1 | 8/1996 |
| CA | 2 528 087 A1 | 12/2004 |
| DE | 107 260 | 7/1974 |
| DE | 124521 | 3/1977 |
| EP | 0 612 758 A1 | 8/1994 |
| EP | 0 646 590 A1 | 4/1995 |
| EP | 0 693 475 A1 | 1/1996 |
| EP | 0 728 768 A2 | 8/1996 |
| EP | 0 729 969 A1 | 9/1996 |
| EP | 0 799 819 A1 | 10/1997 |
| GB | 1 394 542 | 5/1975 |
| JP | 6-90934 B2 | 11/1994 |
| JP | 07-326372 | 12/1995 |
| JP | 8-99939 A | 4/1996 |
| JP | 11-345629 A | 12/1999 |
| JP | 2002-158039 | 5/2002 |
| JP | 33-4417 | 7/2002 |
| JP | 2003-531881 A | 10/2003 |
| JP | 2004-185862 | 7/2004 |
| JP | 39-28242 | 6/2007 |
| KR | 1992-0005187 B | 6/1992 |
| KR | 1999-0078427 A | 10/1999 |
| WO | WO 01/49651 A2 | 7/2001 |
| WO | WO 01/83422 A1 | 11/2001 |
| WO | WO 2004/089920 A2 | 10/2004 |
| WO | WO 2004/108658 A1 | 12/2004 |
| WO | WO 2005/000788 A1 | 1/2005 |

OTHER PUBLICATIONS

Yasuda et al. (J. Org. Chem. 2001, 66, 7741).*
Lucke et al. (English translation of DD 12451) 1977.*
Pohland et al. (J. Am. Chem. Soc., 1955, 77, 2483).*
Tetsuji Kametani et al., "Syntheses of Analgesics. XXVIII, Syntheses of 4-Amino-3-methyl-1,2-diphenyl-2-propionyloxybutane Derivatives" Yakugaku Zhassi, vol. 92, No. 4, 1972, pp. 421-430, XP009074552, Japan p. 424.
Maurilio Tramontini, "Advances in the Chemistry of Mannich Bases", Synthesis, No. 12, 1973, XP002406126, p. 712: table 6.
International Search Report dated Oct. 30, 2007 (Seven (7) pages).
European Office Action dated Nov. 22, 2006 (Seven (7) pages).
Written Opinion of the International Search Authority (Six (6) pages), Oct. 30, 2007.
Lubell, W. D. et al., "α-Amino Acids as Chiral Educts for Asymmetric Products. Alkylation of N-Phenylfluorenyl α-Amino Ketones. Synthesis of Optically Pure α-Alkyl Carboxylic Acids", J. Am. Chem. Soc., vol. 110, No. 22, 1988, pp. 7447-7455, XP002419870.
International Preliminary Report on Patentability including English translation (Eleven (11) pages).
Schmidle et al, J. Am. Chem. Soc., 1995, 77, 4636-4638.
H. Brunner et al., "Handbook of Enantioselective Catalysis with Transition Metal Compounds", vol. I: Products and Catalysts, 1993, VCH, (table of contents). (Three (3) pages).

(Continued)

*Primary Examiner* — Fereydoun G Sajjadi
*Assistant Examiner* — Jennifer C Sawyer
(74) *Attorney, Agent, or Firm* — Hunton & Williams LLP

(57) ABSTRACT

The present invention relates to a process for the preparation of (1R,2R)-3-dimethylamino-1-ethyl-2-methyl-propyl)-phenol.

14 Claims, No Drawings

(56) References Cited

OTHER PUBLICATIONS

L. Guczi et al., "New Frontiers in Catalysis—Proceedings of the 10th International Congress on Catalysis, Budapest, Jul. 19-24, 1992", Studies in Surface Science and Catalysis, 1993, vol. 45, Elsevier Science Publishers B.V., (table of contents). (Twenty-six (26) pages).

M. A. Harmer et al. "Nafion resin-silica nao-composite solid acid catalysts", Green Chemistry, Feb. 8, 2000, pp. 7-14, The Royal Society of Chemistry. (Eight (8) pages).

W. F. Hölderich et al., "Chapter 16 'Zeolites in Organic Syntheses", Studies in Surface Science and Catalysis, 1991, pp. 631-726, vol. 58, Elsevier B.V., (abstract). (One (1) page).

E. N. Jacobsen et al., "Comprehensive Asymmetric Catalysis I-III", Springer, 1999, (table of contents), (Eight (8) pages).

I. V. Kozhevnikov, "Heteropoly Acids and Related Compounds as Catalysts for Fine Chemical Synthesis", Catalysis Reviews: Science and Engineering, 1995, pp. 311-352, vol. 37, No. 2, Marcel Dekker, Inc. (Forty-three (43) pages).

R. Noyori et al., "Asymmetric Hydrogenation", Catalytic Asymmetric Synthesis, 2000, pp. 1-110, Second Edition, Wiley-VCH, Inc., (table of contents). (Five (5) pages).

G. A. Olah et al., "Perfluorinated Resinsulfonic Acid (Nafion-H®) Catalysis in Synthesis", Synthesis, Jul. 1986, pp. 513-531. (Nineteen (19) pages).

X. Song et al., "Sulfated Zirconia-Based Strong Solid-Acid Catalysts: Recent Progress", Catalysis Reviews: Science and Engineering, 1996, pp. 329-412, vol. 38, No. 3, Marcel Dekker, Inc. (Eighty-five (85) pages).

* cited by examiner

PROCESS FOR THE PREPARATION OF (1R,2R)-3-(3-DIMETHYLAMINO-1-ETHYL-2-METHYLPROPYL)-PHENOL

The present invention relates to a process for the preparation of (1R,2R)-3-(3-dimethylamino-1-ethyl-2-methyl-propyl)-phenol.

A class of active ingredients having excellent analgesic effectiveness and very good tolerability are the substituted dimethyl-(3-aryl-butyl)-amine compounds, which are known inter alia from EP 0 693 475. In particular, (1R,2R)-3-(3-dimethylamino-1-ethyl-2-methyl-propyl)-phenol has proven to be a very promising candidate for the development of an analgesic in clinical trials.

An object of the present invention was, therefore, to provide a process which allows for the preparation of (1R,2R)-3-(3-dimethylamino-1-ethyl-2-methyl-propyl)-phenol via a short route with good overall yield under environmentally acceptable conditions.

In particular, in the process of the present invention all stereocenters can be established via substrate control with almost exclusive formation of only a single diastereomer thus sparing elaborate purification steps to separate stereoisomers and costly chiral reagents, catalysts or ligands. As there are not any undesired side products formed in the process of the present invention, each batch can work at its optimal capacity.

The object of the present invention is met by providing a process for preparing (1R,2R)-3-(3-dimethylamino-1-ethyl-2-methyl-propyl)-phenol, or an acid addition salt thereof, comprising the step of (a) reacting a compound of general formula (I),

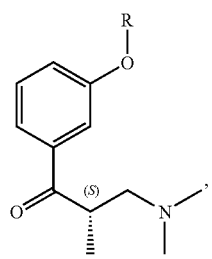
(I)

wherein R represents —$C_{1-6}$-alkyl, —$C_{3-8}$-cycloalkyl, —$C_{1-3}$-alkylene-phenyl, —$C_{1-3}$-alkylene-naphthyl, tetrahydropyranyl or —C(═O)—$C_{1-6}$-alkyl, with ethyl magnesium halide in an inert reaction medium under Grignard conditions.

Preferably R represents methyl, ethyl, n-propyl, isopropyl, n-butyl, isobutyl, tert-butyl, n-pentyl, cyclopropyl, cyclobutyl, cyclopentyl, cyclohexyl, cycloheptyl, benzyl, phenethyl, tetrahydropyranyl, —C(═O)—$CH_3$, —C(═O)—$C_2H_5$, —C(═O)—$CH(CH_3)_2$ or —C(═O)—$C(CH_3)_3$ in the compounds of general formula (I). Particularly preferably R represents methyl, ethyl, cyclopropyl, cyclobutyl, cyclopentyl, cyclohexyl, benzyl, phenethyl, tetrahydropyranyl or —C(═O)—$CH_3$ in the compounds of general formula (I). More particularly preferably R represents methyl, benzyl or tetrahydropyranyl in the compounds of general formula (I).

Yet more preferably R in general formula (I) represents methyl. Thus, very preferably (S)-3-(dimethylamino)-1-(3-methoxyphenyl)-2-methylpropan-1-one is reacted with ethyl magnesium halide in an inert reaction medium under Grignard conditions.

Preferably ethyl magnesium bromide or ethyl magnesium chloride are used as ethyl magnesium halide in step a).

The reaction according to step (a) is preferably carried out in an inert reaction medium, preferably in an organic ether, for example, selected from the group consisting of diethyl ether, tetrahydrofuran, 2-methyltetrahydrofuran, tert-butylmethyl ether or any mixture thereof. The reaction is particularly preferably carried out in tetrahydrofuran with ethyl magnesium chloride at a concentration from 0.5 M to 2 M of the ethyl magnesium chloride. Particularly preferably the reaction is carried out at a concentration of 1 M or 2 M of the ethyl magnesium chloride.

Another object of the present invention is a process for preparing (1R,2R)-3-(3-dimethylamino-1-ethyl-2-methyl-propyl)-phenol, or an acid addition salt thereof, comprising the step of (a) reacting a compound of general formula (I),

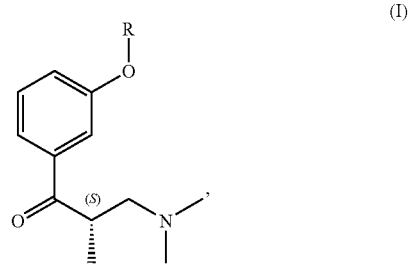
(I)

wherein R represents —$C_{1-6}$-alkyl, —$C_{3-8}$-cycloalkyl, —$C_{1-3}$-alkylene-phenyl, —$C_{1-3}$-alkylene-naphthyl, tetrahydropyranyl or —C(═O)—$C_{1-6}$-alkyl, with ethyl magnesium halide in an inert reaction medium under Grignard conditions, (b) transferring the thus obtained compound of general formula (II),

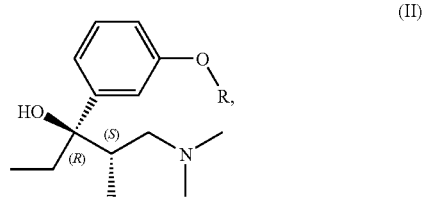
(II)

wherein R has the above defined meaning, to a compound of general formula (III),

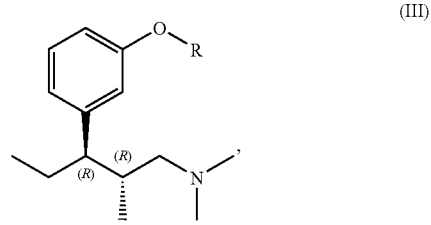
(III)

wherein R has the above defined meaning, optionally in form of an acid addition salt, (c) deprotecting the thus obtained compound of general formula (III) to obtain (1R,2R)-3-(3-dimethylamino-1-ethyl-2-methyl-propyl)-phenol of formula (IV),

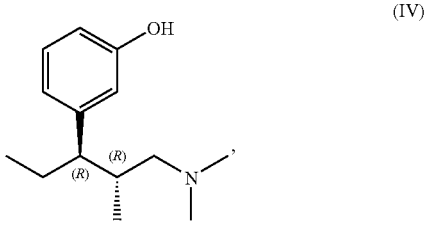

(d) optionally converting the thus obtained (1R,2R)-3-(3-dimethylamino-1-ethyl-2-methyl-propyl)-phenol into an acid addition salt.

Preferably R represents methyl, ethyl, n-propyl, isopropyl, n-butyl, isobutyl, tert-butyl, n-pentyl, cyclopropyl, cyclobutyl, cyclopentyl, cyclohexyl, cycloheptyl, benzyl, phenethyl, tetrahydropyranyl, —C(=O)—CH$_3$, —C(=O)—C$_2$H$_5$, —C(=O)—CH(CH$_3$)$_2$ or —C(=O)—C(CH$_3$)$_3$ in the compounds of general formulae (I), (II) and (III). Particularly preferably R represents methyl, ethyl, cyclopropyl, cyclobutyl, cyclopentyl, cyclohexyl, benzyl, phenethyl, tetrahydropyranyl or —C(=O)—CH$_3$ in the compounds of general formulae (I), (II) and (III). More particularly preferably R represents methyl, benzyl or tetrahydropyranyl in the compounds of general formulae (I), (II) and (III).

Even more particularly preferably R represents methyl in the general formulae (I), (II) and (III). Thus, (S)-3-(dimethylamino)-1-(3-methoxyphenyl)-2-methylpropan-1-one (Ia) is transformed to (1R,2R)-3-(3-dimethylamino-1-ethyl-2-methyl-propyl)-phenol by the following sequence of steps (scheme 1).

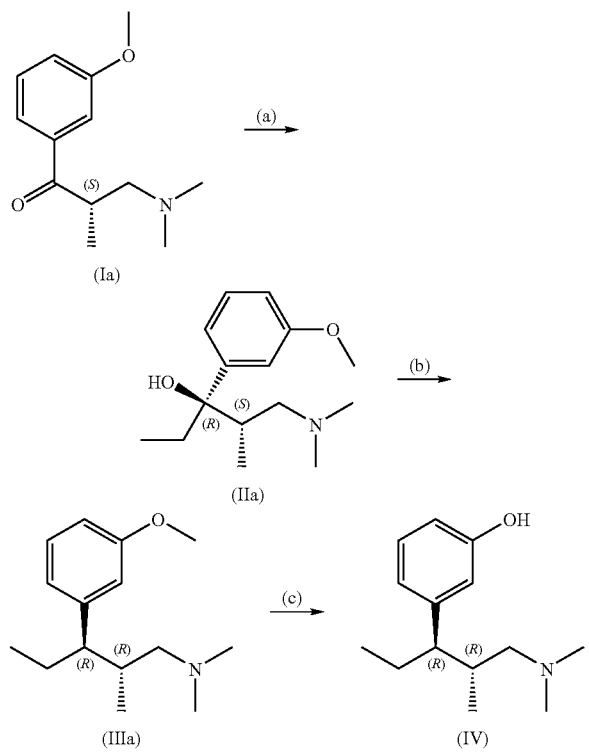

In case R represents methyl in the general formula (III), compound (IIIa) is preferably reacted with hydrobromic acid or methanesulfonic acid and methionine or diisobutylaluminium hydride in a reaction medium, preferably in a reaction medium selected from the group consisting of diethylether, tetrahydrofuran, toluene, 2-methyltetrahydrofuran, dioxane, tert-butyl-methylether and mixtures thereof to yield (1R,2R)-3-(3-dimethylamino-1-ethyl-2-methyl-propyl)-phenol of formula (IV).

In case R represents C$_{1-6}$-alkyl except methyl in the general formula (III), the respective compound of general formula (III) is preferably reacted with hydrobromic acid or diisobutylaluminium hydride in a reaction medium, preferably in a reaction medium selected from the group consisting of diethylether, tetrahydrofuran, toluene, 2-methyltetrahydrofuran, dioxane, tert-butyl-methylether and mixtures thereof to yield (1R,2R)-3-(3-dimethylamino-1-ethyl-2-methyl-propyl)-phenol of formula (IV).

In case R represents tetrahydropyranyl in the general formula (III), the respective compound of general formula (III) is preferably reacted with at least one inorganic acid, preferably with at least one inorganic acid selected from the group consisting of hydrochloric acid, hydrobromic acid, sulfuric acid and phosphoric acid, optionally in the presence of at least one salt, preferably at least one salt selected from the group consisting of ammonium chloride and potassium hydrogensulfate, in a reaction medium, preferably in a reaction medium selected from the group consisting of diethylether, tetrahydrofuran, toluene, 2-methyltetrahydrofuran, dioxane, tert-butyl-methylether, water and mixtures thereof to yield (1R,2R)-3-(3-dimethylamino-1-ethyl-2-methyl-propyl)-phenol of formula (IV).

In case R represents —C$_{3-8}$-cycloalkyl in the general formula (III), the respective compound of general formula (III) is preferably reacted with hydrobromic acid or diisobutylaluminium hydride in a reaction medium, preferably in a reaction medium selected from the group consisting of diethylether, tetrahydrofuran, toluene, 2-methyltetrahydrofuran, dioxane, tert-butyl-methylether and mixtures thereof to yield (1R,2R)-3-(3-dimethylamino-1-ethyl-2-methyl-propyl)-phenol of formula (IV).

In case R represents —C$_{1-3}$-alkylene-phenyl or —C$_{1-3}$-alkylene-naphthyl, a compound of general formula (III) is reacted with hydrobromic acid or diisobutylaluminium hydride in a reaction medium, preferably in a reaction medium selected from the group consisting of diethylether, tetrahydrofuran, toluene, 2-methyltetrahydrofuran, dioxane, tert-butyl-methylether and mixtures thereof or in the presence of hydrogen and at least one catalyst, preferably in the presence of at least one catalyst based on palladium or platinum, more preferably in the presence of palladium on charcoal, in a reaction medium, preferably in a reaction medium selected from the group consisting of diethylether, tetrahydrofuran, toluene, 2-methyltetrahydrofuran, dioxane, tert-butyl-methylether and mixtures thereof to yield (1R,2R)-3-(3-dimethylamino-1-ethyl-2-methyl-propyl)-phenol of formula (IV).

In case R represents —C(=O)—C$_{1-6}$-alkyl in the general formula (III), the respective compound of general formula (III) is preferably reacted with at least one inorganic acid, preferably with at least one inorganic acid selected from the group consisting of hydrochloric acid, hydrobromic acid, sulfuric acid and phosphoric acid, or with at least one inorganic base, preferably with at least one inorganic base selected from the group consisting of sodium hydroxide, potassium hydroxide, sodium carbonate and potassium carbonate in a reaction medium, preferably in a reaction medium selected from the group consisting of diethylether, tetrahydrofuran, toluene, 2-methyltetrahydrofuran, dioxane, tert-butyl-methylether, water and mixtures thereof to yield (1R,2R)-3-(3-dimethylamino-1-ethyl-2-methyl-propyl)-phenol of formula (IV).

In another embodiment of the present invention the agent for deprotecting according to step c) of the inventive process are selected from the group consisting of iodotrimethylsilane, sodium ethyl sulphide, lithium iodide and hydrobromic acid, preferably hydrobromic acid.

The compound (1R,2R)-3-(3-dimethylamino-1-ethyl-2-methyl-propyl)-phenol may be present in form of an acid addition salt, whereby any suitable acid capable of forming such an addition salt may be used.

The conversion of the compound (1R,2R)-3-(3-Dimethylamino-1-ethyl-2-methyl-propyl)-phenol into a corresponding addition salt via reaction with a suitable acid may be effected in a manner well known to those skilled in the art. Suitable acids include but are not limited to hydrochloric acid, hydrobromic acid, sulphuric acid, methanesulfonic acid, formic acid, acetic acid, oxalic acid, succinic acid, tartaric acid, mandelic acid, fumaric acid, lactic acid, citric acid, glutamic acid and aspartic acid. In a preferred embodiment the acid addition salt is the hydrochloride salt.

The salt formation may preferably be effected in a suitable solvent including diethyl ether, diisopropyl ether, alkyl acetates, acetone, 2-butanone or any mixture thereof. Also preferably, reaction with trimethylchlorosilane in a suitable solvent may be used for the preparation of the hydrochloride addition salt.

Preferably a compound of general formula (I) can be obtained by (a') reacting a compound of general formula (V),

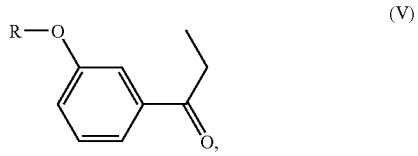

(V)

wherein R represents —$C_{1-6}$-alkyl, —$C_{3-8}$-cycloalkyl, —$C_{1-3}$-alkylene-phenyl, —$C_{1-3}$-alkylene-naphthyl, tetrahydropyranyl or —C(=O)—$C_{1-6}$-alkyl, with dimethylamine hydrochloride and paraformaldehyde in an inert reaction medium under Mannich conditions and
(a") subsequent resolution of the thus obtained compound of general formula (VI),

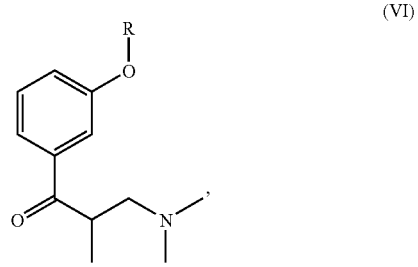

(VI)

wherein R has the above defined meaning.

Preferably R represents methyl, ethyl, n-propyl, isopropyl, n-butyl, isobutyl, tert-butyl, n-pentyl, cyclopropyl, cyclobutyl, cyclopentyl, cyclohexyl, cycloheptyl, benzyl, phenethyl, tetrahydropyranyl, —C(=O)—$CH_3$, —C(=O)—$C_2H_5$, —C(=O)—$CH(CH_3)_2$ or —C(=O)—$C(CH_3)_3$ in the compounds of general formulae (V) or (VI). Particularly preferably R represents methyl, ethyl, cyclopropyl, cyclobutyl, cyclopentyl, cyclohexyl, benzyl, phenethyl, tetrahydropyranyl or —C(=O)—$CH_3$ in the compounds of general formulae (V) or (VI). More particularly preferably R represents methyl, benzyl or tetrahydropyranyl in the compounds of general formulae (V) or (VI).

Even more particularly preferably R represents methyl in the general formulae (V) and (VI). Thus, 1-(3-methoxyphenyl)propan-1-one is converted to 3-(dimethylamino)-1-(3-methoxyphenyl)-2-methylpropan-1-one (VIa) with dimethylamine hydrochloride and paraformaldehyde in an inert reaction medium under Mannich conditions.

Preferably the resolution in step (a") is performed by reacting a compound of general formula (VI) with a chiral acid selected from the group consisting of L-(−)-dibenzoyl tartaric acid, L-(−)-dibenzoyl tartaric acid.$H_2O$ and D-(−)-tartaric acid, subsequent separation of the thus obtained salt and liberation of the corresponding compound of general formula (I) in form of the free base.

It is preferred that the resolution is performed in an alcoholic reaction medium selected from the group consisting of methanol, ethanol, 1-propanol, 2-propanol and any mixture thereof or in a mixture of an alcoholic reaction medium selected from the group consisting of methanol, ethanol, 1-propanol, 2-propanol and acetone.

Preferably transfer according to step (b) is performed by (b') subjecting the compound of general formula (II) to dehydration and (b") hydrogenation of the thus obtained compound of general formula (VII),

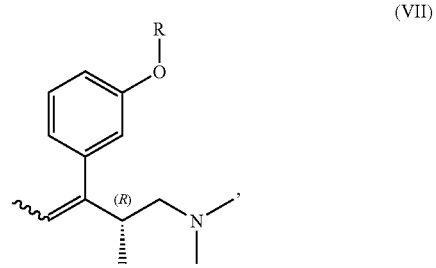

(VII)

wherein R represents —$C_{1-6}$-alkyl, —$C_{3-8}$-cycloalkyl, —$C_{1-3}$-alkylene-phenyl, —$C_{1-3}$-alkylene-naphthyl, tetrahydropyranyl or —C(=O)—$C_{1-6}$-alkyl, using a suitable catalyst in an inert reaction medium in the presence of hydrogen.

Preferably R represents methyl, ethyl, n-propyl, isopropyl, n-butyl, isobutyl, tert-butyl, n-pentyl, cyclopropyl, cyclobutyl, cyclopentyl, cyclohexyl, cycloheptyl, benzyl, phenethyl, tetrahydropyranyl, —C(=O)—$CH_3$, —C(=O)—$C_2H_5$, —C(=O)—$CH(CH_3)_2$ or —C(=O)—$C(CH_3)_3$ in the compound of general formula (II). Particularly preferably R represents methyl, ethyl, cyclopropyl, cyclobutyl, cyclopentyl, cyclohexyl, benzyl, phenethyl, tetrahydropyranyl or —C(=O)—$CH_3$ in the compound of general formula (II).

More particularly preferably R represents methyl, benzyl or tetrahydropyranyl in the compound of general formula (II).

Even more particularly preferably R represents methyl in the compound of general formula (II). Thus, (2S,3R)-1-(dimethylamino)-3-(3-methoxyphenyl)-2-methylpentan-3-ol is transferred to (2R,3R)-3-(3-methoxyphenyl)-N,N,2-trimethylpentan-1-amine by dehydration (step (b')) and subsequent hydrogenation (step (b")).

Preferably the hydrogenation in step (b") is effected via homogeneous catalysis in the presence of hydrogen after the dehydration step (b'). The hydrogen is preferably in gaseous form, although it is also possible for at least part of it to be dissolved in a liquid phase.

Preferably the homogeneous catalyst used for hydrogenation in step (b") according to the present invention is a transition metal complex of rhodium, iridium or ruthenium, particularly preferably a transition metal complex of rhodium or iridium, more particularly a transition metal complex of rhodium with diphosphine ligands.

Diphosphine ligands which can preferably be used are, for example known from the following literature references: a) H. Brunner, W. Zettlmeier, Handbook of Enantioselective Catalysis. VCH Weinheim, 1993, vol. 2; b) R. Noyori et al. in Catalytic Asymmetric Synthesis Second Edition (I. Ojima, Ed.), Wiley-VCH, Weinheim, 2000; c) E. N. Jacobsen, A. Pfaltz, H. Yamamoto (Eds.), Comprehensive Asymmetric Catalysis Vol I-III, Springer Berlin, 1999, and the references cited therein.

Particularly preferably the catalyst is chosen from the group consisting of rhodium (−)-DIPAMP [(R,R)-(−)-1,2-Bis[(2-methoxyphenyl)(phenyl)phosphino]ethane], rhodium (+)-DIPAMP [(S,S)-(+)-1,2-Bis[(2-methoxyphenyl)(phenyl)phosphino]ethane], rhodium R-Solphos [R-(+)-N,N'-Dimethyl-7,7'-bis(diphenylphosphino)-3,3',4,4'-tetrahydro-8,8'-bi-2H-1,4-benzoxazine] and rhodium S-Solphos [S-(−)-N,N'-Dimethyl-7,7'-bis(diphenylphosphino)-3,3',4,4'-tetrahydro-8,8'-bi-2H-1,4-benzoxazine]. The reaction parameters for the homogeneous hydrogenation in step (b"), such as, for example, pressure, temperature or reaction time, can vary over a wide range.

Preferably, the temperature during the homogeneous hydrogenation in step (b") can be in each case from 0 to 250° C., particularly preferably from 10 to 40° C. and very particularly preferably from 15 to 25° C.

The homogeneous hydrogenation in step (b") can preferably be carried out at reduced pressure, at normal pressure or at elevated pressure, preferably in the range from 0.01 to 300 bar. It is particularly preferred to carry out the reactions under pressure in a range from 3 to 20 bar, in particular from 8 to 12 bar.

The reaction time can vary in dependence on various parameters, such as, for example, temperature, pressure, nature of the compound to be reacted or the properties of the catalyst, and can be determined for the process in question by the person skilled in the art using preliminary tests.

The dehydration step (b') is preferably acid-catalysed. Preferably the acid is selected from the group consisting of formic acid, hydrochloric acid, acetic acid, sulfuric acid, hydrobromic acid, methanesulfonic acid or any mixture thereof. It is preferable if the acid is employed in a high concentration. Particularly preferably the concentration of the hydrochloric acid is >20%, preferably >30%, particularly preferably >35% by weight. Alternatively, the acid can also be used in gaseous form.

The compounds of general formula II and VII used in step (b') according to the present invention are preferably in liquid phase and to that end are preferably mixed with or dissolved in a reaction medium that is liquid under the particular reaction conditions.

Examples of suitable reaction media are water, acetic acid, formic acid, toluene, hydrochloric acid, sulfuric acid, hydrobromic acid, methanesulfonic acid or any mixture thereof. Of course, it is also possible to use mixtures or multiphase systems comprising two or more of the above-mentioned liquids in the processes according to the present invention. A reaction in supercritical $CO_2$ as solvent is also possible.

The reaction parameters for the dehydration in step (b'), such as, for example, pressure, temperature or reaction time, can vary over a wide range.

It is preferable if the reaction temperature in step (b') is between 35 and 100° C., particularly preferably 45 and 80° C., more particularly preferably between 50 and 60° C.

The dehydration step (b') can preferably be carried out at reduced pressure, at normal pressure or at elevated pressure, preferably in the range from 0.01 to 300 bar. It is particularly preferred to carry out the reactions under pressure in a range from 0.5 to 5 bar, in particular from 0.5 to 1.5 bar.

The reaction time can vary in dependence on various parameters, such as, for example, temperature, pressure, nature of the compound to be reacted or the properties of the catalyst, and can be determined for the process in question by the person skilled in the art using preliminary tests. It is preferable if the reaction time of step (b') is between 2 and 10 h, particularly preferably between 3 and 8 h, more particularly preferably between 4 and 6 h.

The continuous removal of samples in order to monitor the reaction, for example by means of gas chromatography methods, is also possible, optionally in combination with regulation of the corresponding process parameters.

The concentration of the acid in the reaction medium is preferably 20 to 26 M in case of formic acid, 5 to 18 M in case of acetic acid, 8 to 14 M in case of hydrochloric acid and 4 to 36 M, more preferably 4 to 18 M, in case of sulfuric acid.

The particular compound of general formula (VII) obtained can be isolated and/or purified by conventional methods known to the person skilled in the art.

Alternatively, the dehydration step (b') can also be carried out in the presence of at least one acidic catalyst, which can preferably be selected from the group consisting of ion-exchange resins, zeolites, heteropoly acids, phosphates, sulfates and optionally mixed metal oxides.

The term catalyst within the context of the present invention includes both catalytically active materials themselves and inert materials that are provided with a catalytically active material. Accordingly, the catalytically active material can, for example, be applied to an inert carrier or can be present in a mixture with an inert material. There come into consideration as inert carrier or inert material, for example, carbon and other materials known to the person skilled in the art.

Suitable catalysts and their preparation are known per se to the person skilled in the art, for example from Venuto, P. B., Microporous Mater., 1994, 2, 297; Hölderich, W. F., van Bekkum, H., Stud. Surf. Sci. Catal., 1991, 58, 631, Hölderich, W. F., Proceedings of the 10th International Congress on Catalysis, 1992, Budapest, Guczi, L. et al. (editors), "New Frontiers in Catalysis", 1993, Elsevier Science Publishers, Kozhenikov, I. V., Catal. Rev. Sci. Eng., 1995, 37, 311, Song, X., Sayari, A., Catal. Rev. Sci. Eng., 1996, 38, 329. The corresponding literature descriptions are incorporated herein by reference and form part of the disclosure.

They are suitable for the dehydration in particular those ion-exchange resins that carry sulfonic acid groups are used.

Preference is given to ion-exchange resins based on tetrafluoroethylene/perfluorovinyl ether copolymers, optionally in the form of their silica nanocomposites, as are described, for example, in the literature publications of Olah et al. Synthesis, 1996, 513-531 and Harmer et al. Green Chemistry, 2000, 7-14, the corresponding descriptions of which are incorporated herein by reference and form part of the disclosure. Corresponding products are available commercially, for example under the name Nafion®, and can also be used in that form in the processes according to the present invention.

Preference is further given to ion-exchange resins based on styrene/divinylbenzene copolymers, which can be prepared by conventional processes known to the person skilled in the art.

There come into consideration for the dehydration particularly preferably sulfonic-acid-group-carrying ion-exchange resins based on styrene/divinylbenzene copolymers, as are marketed, for example, under the name Amberlyst® by Rohm & Haas and which can also be used as such in the processes according to the present invention. These ion-exchange resins are distinguished in particular by their stability towards water and alcohols, even at elevated temperatures, for example from 130 to 160° C.

The degree of crosslinking and the structure of these ion-exchange resins can vary. For example, mention may be made of macroporous ion-exchange resins having heterogeneous pore diameter distribution, isoporous ion-exchange resins having virtually uniform pore diameter distribution, or gel-like ion-exchange resins having no or virtually no pores. The macroporous resins in particular can be used with particular advantage for heterogeneous catalysis in the liquid phase.

Particularly suitable macroporous resins having a mean pore diameter of from 20 to 30 nm and a minimum concentration of active groups of from 4.70 to 5.45 equivalents per kg of resin are available commercially under the names Amberlyst® 15, Amberlyst® 35 and Amberlyst® 36 and accordingly can also be used in the processes according to the present invention.

It is likewise preferred to carry out the dehydration in the presence of an acidic catalyst based on metal oxides such as, for example, $SiO_2$, $Al_2O_3$, $TiO_2$, $Nb_2O_5$, $B_2O_3$ or based on mixed metal oxides such as, for example, $Al_2O_3/SiO_2$ or $Al_2O_3/B_2O_3$.

Preferably, the temperature for dehydration (b') when using an acidic catalyst as describe above is in each case from 20 to 250° C., particularly preferably from 50 to 180° C. and very particularly preferably from 100 to 160° C.

The ratio of acidic catalyst and compound of general formula (II) is preferably in the range from 1:200 to 1:1, in particular from 1:4 to 1:2.

After the dehydration, the catalyst can be separated from the reaction mixture in a simple manner, preferably by filtration. The particular compound of general formula (VII) obtained be isolated and/or purified by conventional methods known to the person skilled in the art.

Alternatively, the dehydration step (b') can also be carried out by subjecting a compound of general formula (II) to an excess of thionyl chloride, optionally in a reaction medium, preferably in a reaction medium selected from the group consisting of diethylether, tetrahydrofuran, toluene, 2-methyltetrahydrofuran, dioxane, tert-butyl-methylether and mixtures thereof, and subsequent heating of the thus obtained reaction mixture to 40° C. to 120° C., preferably to 80° C. to 120° C.

The hydrogenation of step (b") can also be effected via heterogeneous catalysis with hydrogen. The hydrogen is preferably in gaseous form, although it is also possible for at least part of it to be dissolved in a liquid phase.

Heterogeneous catalysis within the context of the present invention means that the catalysts used in step (b") are in each case present in the solid state of aggregation.

Preferably the heterogeneous catalyst used for hydrogenation in step (b") according to the present invention contains one or more transition metals, these metals can preferably be selected from the group consisting of Cu, Ag, Au, Zn, Cd, Hg, V, Nb, Ta, Cr, Mo, W, Fe, Ru, Os, Co, Rh, Ir, Ni, Pd, Pt, particularly preferably from the group consisting of Ru, Rh, Pd, Pt and Ni.

The corresponding catalysts can preferably contain one or more of the above-mentioned transition metals in the same or different oxidation states. It may also be preferable for the corresponding catalysts to contain one or more of the above-mentioned transition metals in two or more different oxidation states.

The preparation of catalysts doped with transition metals can be carried out by conventional processes known to the person skilled in the art.

Preferably the catalyst used for hydrogenation in step (b") is selected from the group consisting of Raney nickel, palladium, palladium on carbon (1-10 wt. %, preferably 5 wt. %), platinum, platinum on carbon (1-10 wt. %, preferably 5 wt. %), ruthenium on carbon (1-10 wt. %, preferably 5 wt. %) and rhodium on carbon (1-10 wt. %, preferably 5 wt. %), more preferably palladium on carbon (1-10 wt. %, preferably 5 wt. %) is used as the catalyst for hydrogenation in step (b").

The compounds of general formula VII or III used in step (b") according to the present invention are preferably in liquid phase and to that end are preferably mixed with or dissolved in a reaction medium that is liquid under the particular reaction conditions.

Examples of suitable reaction media are methanol, ethanol, isopropanol, n-butanol, n-propanol, toluene, heptane, hexane, pentane, acetic acid, ethyl acetate, formic acid, hydrochloric acid, hydrobromic acid, sulfuric acid and mixtures thereof. More preferably ethanol is used as the reaction medium in step (b"). Of course, it is also possible to use mixtures or multiphase systems comprising two or more of the above-mentioned liquids in the processes according to the present invention. A reaction in supercritical $CO_2$ as solvent is also possible.

The reaction parameters for the heterogeneous hydrogenation in step (b"), such as, for example, pressure, temperature or reaction time, can vary over a wide range both.

Preferably, the temperature during the heterogeneous hydrogenation in step (b") is in each case from 0 to 250° C., particularly preferably from 15 to 180° C. and very particularly preferably from 15 to 30° C.

The heterogeneous hydrogenation in step (b") can preferably be carried out at reduced pressure, at normal pressure or at elevated pressure, preferably in the range from 1 to 300 bar. It is particularly preferred to carry out the reactions under pressure in a range from 2 to 10 bar, in particular from 4 to 10 bar.

The reaction time can vary in dependence on various parameters, such as, for example, temperature, pressure, nature of the compound to be reacted or the properties of the catalyst, and can be determined for the process in question by the person skilled in the art using preliminary tests.

The continuous removal of samples in order to monitor the reaction, for example by means of gas chromatography methods, is also possible, optionally in combination with regulation of the corresponding process parameters.

The total amount of the catalyst(s) used depends on various factors, such as, for example, the ratio of the catalytically active component to any inert material present, or the nature of the surface of the catalyst(s). The optimal amount of catalyst(s) for a particular reaction can be determined by the person skilled in the art using preliminary tests.

The particular compound of general formula (III) obtained can be isolated and/or purified by conventional methods known to the person skilled in the art.

In another embodiment of the invention step b) (scheme 1) is a direct replacement reaction of the OH group by H, preferably carried out in a one-pot reaction. More preferably an OH⁻ is replaced by H⁻.

The steps according to the present invention can each be carried out discontinuously (batchwise) or continuously, preference being given to the discontinuous procedure.

There come into consideration as the reactor for the discontinuous procedure, for example, a slurry reactor, and for the continuous procedure a fixed-bed reactor or loop reactor.

In the following a process for the preparation of (1R,2R)-3-(3-dimethylamino-1-ethyl-2-methyl-propyl)-phenol hydrochloride is described.

EXAMPLE

Preparation of (1R,2R)-3-(3-dimethylamino-1-ethyl-2-methyl-propyl)-phenol hydrochloride

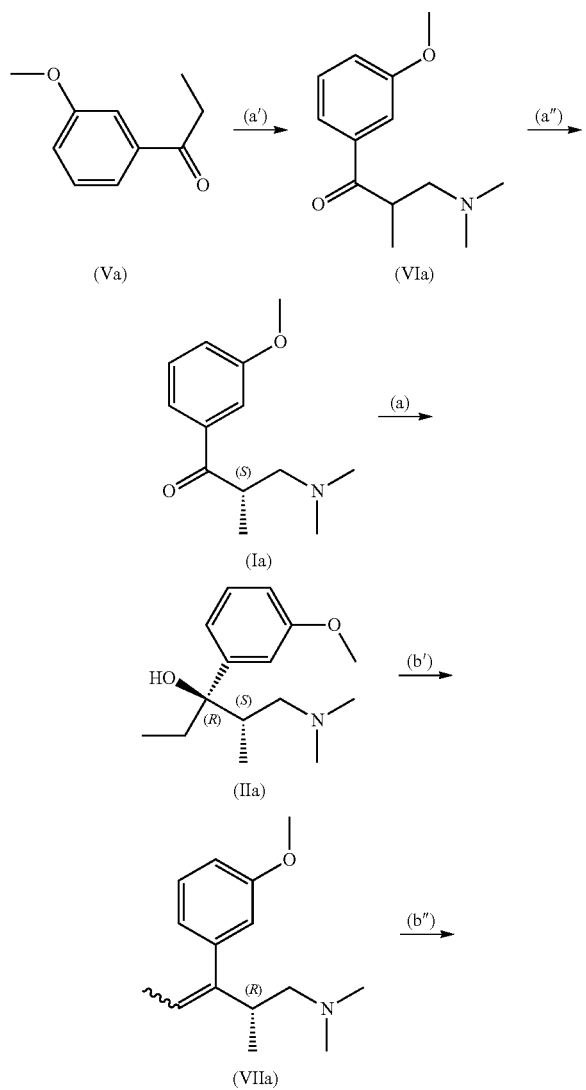

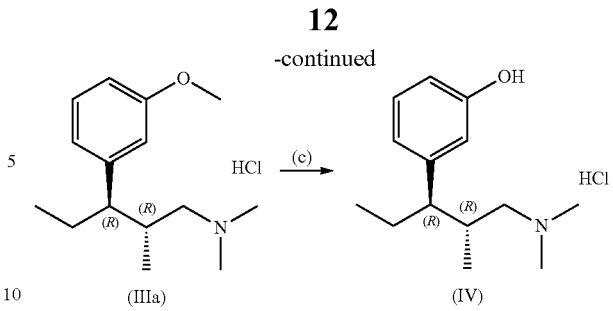

Step (a'): Preparation of 3-(dimethylamino)-1-(3-methoxyphenyl)-2-methylpropan-1-one (VIa)

1-(3-Methoxyphenyl)propan-1-one (16.42 kg, 100 mol), dimethylamine hydrochloride (8.97 kg, 110 mol), paraformaldehyde (3.30 kg, 110 mol) and aqueous hydrochloric acid (32% by weight, 1.14 kg) were dissolved in ethanol under a nitrogen atmosphere in a 100 L (L=liter) double jacket vessel equipped with an electrical impeller stirrer, a gas transition line, Pt100 temperature measuring equipment and an oil based cooling/heating system. The reaction mixture was refluxed for 16 hours, cooled to 25° C. within 3.5 hours and stirred for 1 hour at that temperature. The suspension was separated via a centrifuge and washed three times with 7 L acetone each. 3-(Dimethylamino)-1-(3-methoxyphenyl)-2-methylpropan-1-one hydrochloride was dissolved in water (12.5 L) and tert-butyl-methyl-ether (8.5 L) and stirred at room temperature.

Aqueous sodium hydroxide solution (32% by weight) was added until a pH value between 10.0 and 10.5 was reached and the phases were allowed to separate. The organic phase was distilled off under reduced pressure until at a temperature of 40° C. a pressure of 5 mbar was reached. 3-(Dimethylamino)-1-(3-methoxyphenyl)-2-methylpropan-1-one was obtained as a pale yellow oil (20.75 kg, 94%) that was used in the next step without further purification.

Step (a"): Preparation of (S)-3-(dimethylamino)-1-(3-methoxyphenyl)-2-methylpropan-1-one (Ia)

1. a. Preparation of (S)-3-(dimethylamino)-1-(3-methoxyphenyl)-2-methylpropan-1-one (2R,3R)—O,O'-dibenzoyltartrate in acetone (2R,3R)—O,O'-Dibenzoyl tartaric acid monohydrate (189.1 g, 0.5 mol) was dissolved in acetone (550 mL) in a 2 L reaction plant equipped with a mechanical stirrer, temperature measuring equipment and an oil bath and 3-(dimethylamino)-1-(3-methoxyphenyl)-2-methylpropan-1-one (110.6 g, 0.5 mol) was added. The reaction mixture was heated to 35° C. to 40° C. for 27 hours and allowed to cool to 25° C. The suspension was siphoned off and (S)-3-(dimethylamino)-1-(3-methoxyphenyl)-2-methylpropan-1-one (2R,3R)—O,O'-dibenzoyltartrate was obtained as a colorless solid (233.2 g, 80.5%, ee 96.9%, ee=enantiomeric excess).

1. b. Preparation of (S)-3-(dimethylamino)-1-(3-methoxyphenyl)-2-methylpropan-1-one (2R,3R)—O,O'-dibenzoyltartrate in acetone/methanol (2R,3R)—O,O'-Dibenzoyl tartaric acid monohydrate (2.1 kg, 5.5 mol) was dissolved in a mixture of methanol (555 mL) and acetone (3340 mL) in a 10 L double jacket vessel equipped with an electrical impeller stirrer, a gas transition line, Pt100 temperature measuring equipment and an oil based cooling/heating system and 3-(dimethylamino)-1-(3-methoxyphenyl)-2-methylpropan-1-one (1.23 kg, 5.56 mol) was added. The reaction mixture was heated to 35° C. to 40° C. for 24 hours and allowed to cool to 25° C. The suspension was siphoned off and (S)-3-(dimethylamino)-1-(3-methoxyphenyl)-2-methylpropan-1-one (2R,3R)—O,O'-dibenzoyltartrate was obtained as a colorless solid (2.38 kg, 74%, ee 98.4%).

2. Preparation of (S)-3-(dimethylamino)-1-(3-methoxyphenyl)-2-methylpropan-1-one (Ia)

(S)-3-(Dimethylamino)-1-(3-methoxyphenyl)-2-methylpropan-1-one (2R,3R)—O,O'-dibenzoyltartrate (968 g, 1.67 mmol, ee 98%) was suspended in tert-butylmethyl ether (6 L) in a 10 L double jacket vessel equipped with an electrical impeller stirrer, a gas transition line, Pt100 temperature measuring equipment and an oil based cooling/heating system and diethylamine (384 g, 5.25 moo) was added. The reaction mixture was stirred at 20° C. to 25° C. for 90 minutes and a solid was siphoned off. The filtrate was concentrated at a temperature of 40° C. in vacuo until a pressure of 4 mbar was reached. (S)-3-(dimethylamino)-1-(3-methoxyphenyl)-2-methylpropan-1-one was obtained as a colorless oil (356.7 g, 96.5%, ee 98%).

Step (a): Preparation of (2S,3R)-1-(dimethylamino)-3-(3-methoxyphenyl)-2-methylpentan-3-ol (IIa)

1. Magnesium turnings (93.57 g, 3.85 mol) were suspended in dry ethyl ether (2 L) in a 10 L double jacket vessel equipped with an electrical impeller stirrer, a gas transition line, Pt100 temperature measuring equipment and an oil based cooling/heating system and ethyl bromide (25 g, 0.23 mol) was added. After the reaction has started further ethyl bromide (438.6 g, 4.02 mol) was added within 90 minutes below a temperature of 35° C. and the reaction mixture was stirred for another hour. The reaction mixture was cooled to 10° C. to 15° C., (S)-3-(dimethylamino)-1-(3-methoxyphenyl)-2-methylpropan-1-one (774.6 g, 3.5 mol, ee 98%) dissolved in diethyl ether (0.8 L) was added and the reaction mixture was stirred for another two hours. The reaction mixture was cooled to 5° C. and aqueous ammonium hydrogensulfate solution (10% by weight, 2 L) was added. The phases were separated and the organic phase was concentrated in vacuo at 40° C. until a pressure of 5 mbar was reached. (2S,3R)-1-(Dimethylamino)-3-(3-methoxyphenyl)-2-methylpentan-3-ol (862.3 g, 98%) was obtained as a colorless oil (ee 98%).

2. (S)-3-(Dimethylamino)-1-(3-methoxyphenyl)-2-methylpropan-1-one (774.6 g, 3.5 mol, ee 95%) was dissolved in dry tetrahydrofuran (800 mL) in a 10 L double jacket vessel equipped with an electrical impeller stirrer, a gas transition line, Pt100 temperature measuring equipment and an oil based cooling/heating system and ethyl magnesium bromide (2 L, 2 M in THF) was added at a temperature of 15° C. within 2 hours. The reaction mixture was stirred for two hours at that temperature, cooled to 5° C. and aqueous ammonium hydrogen sulfate solution (10% by weight, 2 L) was added. The phases were separated and the organic phase was concentrated in vacuo at 40° C. until a pressure of 5 mbar was reached. (2S,3R)-1-(Dimethylamino)-3-(3-methoxyphenyl)-2-methylpentan-3-ol (871.1 g, 99%) was obtained as a colorless oil (ee 95%).

Step (b'): Preparation of (R)-3-(3-methoxyphenyl)-N,N,2-trimethylpent-3-en-1-amine (VIIa)

1. (2S,3R)-1-(Dimethylamino)-3-(3-methoxyphenyl)-2-methylpentan-3-ol (754.1 g, 3 mol, ee 95%) were dissolved in acetone (5 L) in a 10 L double jacket vessel equipped with an electrical impeller stirrer, a gas transition line, Pt100 temperature measuring equipment and an oil based cooling/heating system. Hydrogen chloride (110 g, 3.0 mol) was transferred within 15 minutes at a temperature of 15° C. through the reaction mixture. The reaction mixture was cooled to 0° C. to 5° C. and after 24 hours at that temperature siphoned off. The product was stored at 40° C. and 10 mbar for 14 hours in a drying oven. (2S,3R)-1-(Dimethylamino)-3-(3-methoxyphenyl)-2-methylpentan-3-ol hydrochloride was obtained as a colorless solid (722.3 g, 83.7%, ee 100%).

2. (2S,3R)-1-(Dimethylamino)-3-(3-methoxyphenyl)-2-methylpentan-3-ol hydrochloride obtained as described above was put into a 250 mL three necked flask equipped with a thermometer, a mechanical compressed air stirrer, reflux condenser and oil bath and aqueous hydrogen chloride solution (150 mL, 36% by weight) was added. The reaction mixture was heated to 55° C. for 5 hours and allowed to cool to 20° C. Aqueous sodium hydroxide solution (33% by weight) was added while cooling until a pH value of 11 was reached. Ethyl acetate (150 mL) was added, the reaction mixture was stirred for 10 minutes, the phases were separated and ethyl acetate was removed in vacuo at 60° C. until a pressure of 10 mbar was reached. (R)-3-(3-Methoxyphenyl)-N,N,2-trimethylpent-3-en-1-amine (21 g, 90%) was obtained as an oily residue (Z/E ratio 4.5:1).

Step (b"): Preparation of (2R,3R)-3-(3-methoxyphenyl)-N,N,2-trimethylpentan-1-amine hydrochloride (IIIa)

1. (R)-3-(3-Methoxyphenyl)-N,N,2-trimethylpent-3-en-1-amine (5 kg, 21.43 mmol) was dissolved in dry ethanol (13 L) at a temperature of 25° C. and rotational stirring frequency of 850±150 per minute in a double jacket hydrogenation apparatus equipped with a stationary mounted lid having a hydrogen and nitrogen supply, electric gassing stirrer, Pt100 temperature measuring equipment, inspecting glass and gas controller "Büchi bpc". The hydrogenation apparatus was flooded with nitrogen. Palladium on charcoal (375 g, 5% by weight) was suspended in aqueous hydrogen chloride (675 g, 32% by weight) and added to the reaction mixture. The hydrogenation apparatus was flooded again with nitrogen and the reaction was carried out at a primary pressure of hydrogen of 5 bar and an internal hydrogen pressure of 1 bar until the reaction was complete. The hydrogenation apparatus was flooded with nitrogen and the catalyst was filtered off on a one layered filter with filtering earth. The filtrate was concentrated in vacuo. The residue was take up in ethyl acetate and aqueous sodium hydroxide (10% by weight, 3.7 L) was added at 20° C. until a pH value of 10 to 12 was reached. The organic phase was concentrated in vacuo at 45° C. to 50° C. until a pressure of 5 mbar was reached. The oily residue was a mixture of (2R,3R)-3-(3-methoxyphenyl)-N,N,2-trimethylpentan-1-amine and (2R,3S)-3-(3-methoxyphenyl)-N,N,2-trimethylpentan-1-amine (4.5 kg, 95%, ratio 5.5 (R,R):1 (R,S)).

2. A mixture of (2R,3R)-3-(3-methoxyphenyl)-N,N,2-trimethylpentan-1-amine and (2R,3S)-3-(3-methoxyphenyl)-N,N,2-trimethylpentan-1-amine (10 kg, 42.56 mol, ratio 5.5: 1) was dissolved in acetone (50 L) in a 100 L double jacket vessel equipped with an electrical impeller stirrer, a gas transition line, Pt100 temperature measuring equipment and an oil based cooling/heating system. Hydrogen chloride (1.55 kg, 42.51 mol) was transferred within 15 minutes at a temperature of 5° C. to 25° C. through the reaction mixture. The reaction mixture was cooled to 0° C. to 5° C. and centrifuged after 2 hours of stirring. The humid solid was put into a stirring vessel, acetone (30 L) was added and the reaction mixture was heated to reflux for 15 minutes. After cooling to 15° C. to 20° C. the product was centrifuged and stored at 40° C. to 50° C. and 150 mbar for 14 hours in a drying oven. (2R,3R)-3-(3-Methoxyphenyl)-N,N,2-trimethylpentan-1-amine hydrochloride (7.17 kg, 63%) was obtained as a colorless solid with a diastereomeric excess of 100%.

Step (c): Preparation of (1R,2R)-3-(3-dimethylamino-1-ethyl-2-methyl-propyl)-phenol hydrochloride (IV)

1. (2R,3R)-3-(3-Methoxyphenyl)-N,N,2-trimethylpentan-1-amine hydrochloride (5 kg, 18.4 mol) was dissolved in methane sulfonic acid (19.5 L) in a 100 L double jacket vessel equipped with an electrical impeller stirrer, a gas transition line, Pt100 temperature measuring equipment and an oil based cooling/heating system and methionine (3.35 kg, 22.5 mol) was added. The reaction mixture was stirred at a temperature of 75° C. to 80° C. for 16 hours, cooled to 15° C. to 25° C. and water (12.5 L) was slowly added at that temperature. Aqueous sodium hydroxide solution (ca. 28 L, 32% by weight) was added until a pH value of 10 to 12 was reached while the temperature was kept below 50° C. Ethyl acetate (15 L) was added and the reaction mixture was stirred for 15 minutes at a rotational stirring frequency of 150 per minute. The phases were separated and the organic phase was washed with water (15 L). Activated charcoal (0.05 kg) was added to the organic phase and filtered off after 30 minutes of stirring. The solvent was removed in vacuo at a temperature of 40° C. to 50° C. until a pressure of 50 mbar was reached. The residue was used in the next step without further purification.

2. The residue obtained as described above was dissolved in acetone (25 L) while stirring and hydrogen chloride (0.78 kg, 21.4 mol) was transferred through the reaction mixture at a temperature of 20° C. to 25° C. The suspension was stirred for 3 hours at a temperature of 0° C. to 5° C. and centrifuged. Isopropanol (35 L) was added to the humid solid in a reaction vessel and the reaction mixture was heated to reflux for 15 minutes. The reaction mixture was cooled to 0° C. to 5° C. and stirred for 3 hours at that temperature. After centrifugation the product was stored at 30° C. to 40° C. and 150 mbar for 16 hours in a drying oven. (1R,2R)-3-(3-Dimethylamino-1-ethyl-2-methyl-propyl)-phenol hydrochloride (4.18 kg, 88%) were obtained as a colorless solid with a purity of 100%.

The invention claimed is:
1. A process for preparing (1R,2R)-3-(3-dimethylamino-1-ethyl-2-methyl-propyl)-phenol, or an acid addition salt thereof, said process comprising:
(a') reacting a compound corresponding to formula (V):

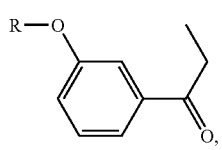

(V)

wherein R represents —$C_{1-6}$-alkyl, —$C_{3-8}$-cycloalkyl, —$C_{1-3}$-alkylene-phenyl, —$C_{1-3}$-alkylene-naphthyl, tetrahydropyranyl or —C(=O)—$C_{1-6}$-alkyl,
with dimethylamine hydrochloride and paraformaldehyde in an inert reaction medium under Mannich conditions to yield a compound of formula (VI),

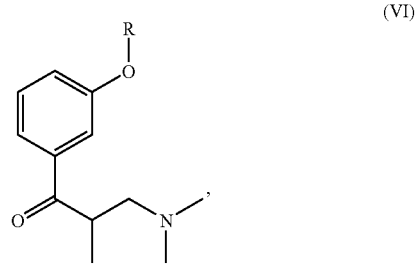

(VI)

wherein R has the above defined meaning; and
(a") subsequently resolving the compound of formula (VI), wherein the resolution is carried out by:
(i) reacting a compound of formula (VI) with a chiral acid selected from the group consisting of L-(−)-dibenzoyl tartaric acid and L-(−)-dibenzoyl tartaric acid $H_2O$ to yield a salt,
(ii) separating the salt, and
(iii) liberating the corresponding compound of formula (I) in the form of a free base, to yield a compound of formula (I)

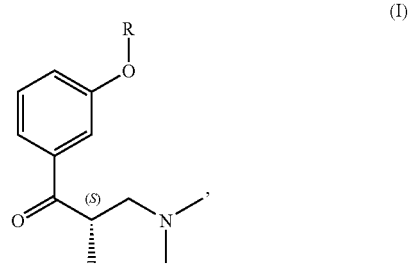

(I)

wherein R has the above defined meaning,
(a) reacting the compound corresponding to formula (I), with an ethyl magnesium halide in an inert reaction medium under Grignard conditions to yield a compound corresponding to formula (II):

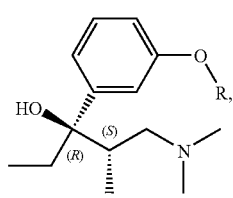

(II)

wherein R has the above defined meaning,
(b) converting the compound of formula (II) to a compound corresponding to formula (III):

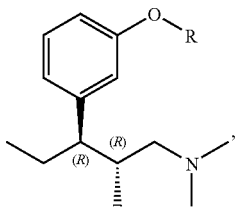

wherein R has the above defined meaning, optionally in form of an acid addition salt, wherein the conversion is carried out by:
(b') dehydrating the compound of formula (II) to yield a compound corresponding to formula (VII):

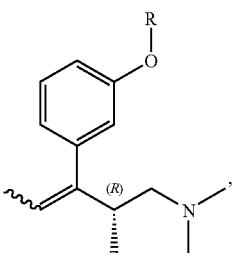

wherein R has the above defined meaning; and
(b") hydrogenating the compound of formula (VII) using a catalyst in an inert reaction medium in the presence of hydrogen to yield a compound of formula (III),
(c) deprotecting the compound of formula (III) to yield (1R,2R)-3-(3-dimethylamino-1-ethyl-2-methyl-propyl)-phenol corresponding to formula (IV):

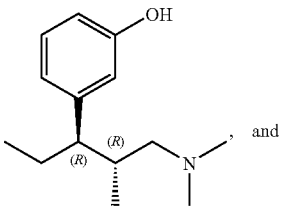

and (d) optionally converting the (1R,2R)-3-(3-dimethylamino-1-ethyl-2-methyl-propyl)-phenol from (c) into an acid addition salt.

2. A process according to claim 1, wherein R represents methyl, ethyl, n-propyl, isopropyl, n-butyl, isobutyl, tert-butyl, n-pentyl, cyclopropyl, cyclobutyl, cyclopentyl, cyclohexyl, cycloheptyl, benzyl, phenethyl, tetrahydropyranyl, —C(=O)—CH$_3$, —C(=O)—C$_2$H$_5$, —C(=O)—CH(CH$_3$)$_2$ or —C(=O)—C(CH$_3$)$_3$.

3. A process according to claim 2, wherein R represents methyl, ethyl, cyclopropyl, cyclobutyl, cyclopentyl, cyclohexyl, benzyl, phenethyl, tetrahydropyranyl or —C(=O)—CH$_3$.

4. A process according to claim 3, wherein R represents methyl, benzyl or tetrahydropyranyl.

5. A process according to claim 1, wherein said ethyl magnesium halide is ethyl magnesium chloride or ethyl magnesium bromide.

6. A process according to claim 1, wherein the inert reaction medium is selected from the group consisting of diethyl ether, tetrahydrofuran, 2-methyltetrahydrofuran, tert-butyl-methylether, diisopropylether, and mixtures thereof.

7. A process according to claim 1, wherein the resolution is carried out in an alcoholic reaction medium selected from the group consisting of methanol, ethanol, 1-propanol, 2-propanol, and mixtures thereof.

8. A process according to claim 1, wherein the hydrogenation in (b") is effected by homogeneous catalysis.

9. A process according to claim 1, wherein the dehydration in (b') is acid-catalyzed.

10. A process according to claim 9, wherein the dehydration is catalyzed by an acid selected from the group consisting of formic acid, hydrochloric acid, sulfuric acid, methanesulfonic acid, hydrobromic acid, and mixtures thereof.

11. A process according to claim 1, wherein the hydrogenation in (b") is effected via heterogeneous catalysis.

12. A process according to claim 11, wherein the catalyst used for hydrogenation is selected from the group consisting of Raney nickel, palladium, palladium on carbon, platinum, platinum on carbon, ruthenium on carbon, and rhodium on carbon.

13. A process according to claim 1, wherein step b) is a direct replacement reaction of the OH group by H.

14. A process according to claim 13, wherein said direct replacement is carried out in a one-pot reaction.

* * * * *